(12) United States Patent
Filteau et al.

(10) Patent No.: US 8,318,615 B1
(45) Date of Patent: Nov. 27, 2012

(54) LAUNDERABLE, LEAK-PROOF, BREATHABLE FABRIC AND ARTICLES MADE THEREFROM

(75) Inventors: Martin Filteau, St-Hyacinthe (CA); Rene Nantel, St-Hyacinthe (CA); Yun Shao, Brossard (CA)

(73) Assignee: Tri-Sis Inc., Lunenburg, Ontario (CA)

(*) Notice: Subject to any disclaimer, the term of this patent is extended or adjusted under 35 U.S.C. 154(b) by 0 days.

(21) Appl. No.: 10/149,635

(22) PCT Filed: Nov. 10, 2000

(86) PCT No.: PCT/CA00/01338
§ 371 (c)(1),
(2), (4) Date: Nov. 4, 2002

(87) PCT Pub. No.: WO01/34080
PCT Pub. Date: May 17, 2001

(51) Int. Cl.
*B32B 5/18* (2006.01)
(52) U.S. Cl. ............ 442/77; 428/86; 428/91; 442/59; 442/76
(58) Field of Classification Search ............ 428/86, 428/91; 442/59, 76, 77
See application file for complete search history.

(56) References Cited

U.S. PATENT DOCUMENTS

| | | | | |
|---|---|---|---|---|
| 3,616,150 A | * | 10/1971 | Borge | 428/193 |
| 3,650,880 A | * | 3/1972 | Tieniber | 442/76 |
| 3,852,947 A | * | 12/1974 | Mayer | 57/245 |
| 3,860,469 A | * | 1/1975 | Gregorian et al. | 156/83 |
| 4,360,015 A | * | 11/1982 | Mayer | 602/47 |
| 4,761,324 A | * | 8/1988 | Rautenberg et al. | 428/198 |
| 4,803,116 A | * | 2/1989 | Amano et al. | 442/63 |
| 4,808,675 A | * | 2/1989 | Twilley et al. | 525/408 |
| 5,142,750 A | * | 9/1992 | Dyer et al. | 26/29 R |
| 5,204,156 A | * | 4/1993 | Lumb et al. | 428/96 |
| 5,244,716 A | * | 9/1993 | Thornton et al. | 428/198 |
| 5,439,438 A | * | 8/1995 | Ersfeld et al. | 602/3 |
| 5,584,801 A | * | 12/1996 | Kuroyanagi et al. | 602/47 |
| 6,160,196 A | * | 12/2000 | Knieler et al. | 602/48 |
| 6,368,687 B1 | * | 4/2002 | Joseph et al. | 428/40.1 |

OTHER PUBLICATIONS

Celanese Acetate LLC, Complete Textile Glossary, 2001, cover, copyright, foreward, pp. 22 and pp. 104.*

* cited by examiner

*Primary Examiner* — Peter Y Choi
(74) *Attorney, Agent, or Firm* — Hodgson Russ LLP (57) ABSTRACT

A launderable and reusable, leak-proof, breathable fabric and, more specifically, a composite fabric comprised of a liquid absorptive layer and a liquid impervious but vapor permeable layer. Such fabric is useful in drawing fluids, such as bodily fluids, away from a source, such as the body, and retaining them within the absorptive layer while evaporation thereof takes place though the vapor permeable layer. This material consists of two juxtaposed layers. The inner layer has the characteristic of being liquid permeable so as to allow the body fluids to flow into it and be absorbed. The outer layer has the characteristic of being liquid impermeable but air or vapor permeable, so that the liquid absorbed in the inner layer does not strike through the outer layer.

39 Claims, 3 Drawing Sheets

Fig. 1 Absorption vs. Retention in the Test Materials

LAUNDERABLE, LEAK-PROOF, BREATHABLE FABRIC AND ARTICLES MADE THEREFROM

FIELD OF THE INVENTION

The invention relates to a launderable/reusable, leak-proof, breathable fabric and, more specifically, to a composite fabric comprised of a liquid absorptive layer and a liquid impervious but vapour permeable layer, as well as articles made therefrom. Such fabric is useful in drawing fluids away from a source and retaining them within the absorptive layer while evaporation thereof takes place though the vapour permeable layer.

BACKGROUND OF THE INVENTION

There are innumerous situations wherein the emission of bodily fluids presents problems in day-to-day life. Types of bodily fluid include, but are not necessarily limited to: perspiration, menstrual flow and other vaginal discharges, urine and fecal emissions, salivation and nasal emissions, lactation in nursing females, and nocturnal emissions. Involuntary emissions often lead to embarrassing situations where they exude through and are visible on clothing and/or result in transmission of odours. Many proposals have been offered for dealing with these problems and these can be categorized broadly into solutions involving emissions of large or small volumes. Large volume emissions such as infant urinary and fecal excretions, incontinence and heavy menstrual flow typically require the use of highly absorbent materials, for example in the form of diapers for both adults and infants, and feminine hygienic products such as tampons, pads and liners, to retain the emitted matter until the absorbent can be removed and, if necessary, replaced. Oftentimes, such products are disposable for convenience or because the absorption changes the structure of the product so that it cannot be reused. Typically, these products are relatively conspicuous due to their bulk or noise they might generate (i.e. in the case of adult diapers) when moving about.

Smaller volume emissions involving light menstrual flow or excreta are sometimes also handled in similar manners. When emissions are expected in cases involving mild intermittent incontinence or nearing the commencement of the menstrual cycle, such products are typically used as a precaution merely to avoid the consequences. When no emissions occur, the article is still disposed of for hygienic reasons which results in unnecessary costs to the consumer and an additional burden on our environment, even where the products are biodegradable.

The prior art reveals that there are numerous products designed for collecting and maintaining women's menstrual flow or body fluid of incontinence and reference may be made to the following U.S. Pat. Nos. 5,429,627 dated Jul. 4, 1995 to Johnson et al; 5,429,311 dated Jul. 4, 1995 to Tel-Aviv et al; 4,678,465 dated Jul. 7, 1987 to Avejic; 5,069,672 dated Dec. 3, 1991 to Wippler et al; 5,368,585 dated Nov. 29, 1994 to Dokken; 5,342,340 dated Aug. 30, 1994 to Kichefski; and 5,261,901 dated Nov. 16, 1993 to Guay. The products described in these patents are designed for use with different magnitude of flow or leakage, which frequently cause embarrassing markings (strike-through) and/or troublesome clean-ups. Moreover, there are periods of time when there is uncertainty as to whether light flow, not only menstrual flow but discharge due to incontinence, may occur when pads or tampon type products are not being worn.

While mild perspiration is typically evaporated through many clothing fabrics, heavy perspiration can wet materials and thereby become visible and leave perspiration stains after evaporating from the cloth. Washable or disposable panels are often attached to clothing articles to absorb these minor emissions such as, for example, armpit panels to absorb excess perspiration and inserts for nursing bras.

Nighttime emissions (i.e. during sleep) can result in soiled or wetted bedding. The bodily fluids may soak through the linen and into the mattress or may become trapped against the person's skin for a long period of time before the person wakes up, which may result in skin irritation and increased odour. Where emissions during sleep are expected, it is often the solution to provide so-called "rubber sheets" which tend to be both liquid and vapour impermeable. While such solutions prevent the emissions from soaking into the mattress, they do not necessarily permit ready evaporation of the liquid.

In the medical field, it would be useful to have a protective garment which prevents bodily fluids from others which might come into contact with the garment from being transmitted through the garment yet which enables certain bodily fluids of the wearer, such as perspiration, to be evaporated.

Research has showed that there are numerous publications and patents on absorbent diapers, napkins and pads for incontinence, all of which are designed to be disposed once soiled. However, there has been little progress towards non-disposable or launderable absorbent undergarments or materials therefor. E. Lees [Wuagneux Nonwovens Industry 28/9, p 104-106, 1997] found that the sales of absorbent underwear have been rising in the adult incontinence market. There have also been some new innovations in the market, including an absorbent undergarment like regular underwear, which is expected to attain increased sales in the future. There is also a growing trend in odour control products.

As mentioned above, a hygienic absorbent undergarment must be capable of preventing leakage or strike through from body fluid flows which are not necessarily of great quantity and be of great comfort. Accordingly, a primary distinguishing feature of a reusable undergarment would be in the use of special materials to maintain a high degree of comfort for the wearer as well as the necessary structural and functional integrity to endure multiple cycles of use and washing. For example, while the thickness of reusable diapers typically range from 2.0 to 2.5 mm and even up to 5.0 mm, a material for an absorbent undergarment should be on the order of 0.5-1.5 mm to not only remain inconspicuous, but to be visually equivalent to normal wear undergarments.

Preferably, these garments should be virtually indistinguishable from normal undergarments in both comfort, wearability, durability, and style.

In the market, there exist reusable absorbent undergarments consisting of two layers or three layers. Two layer undergarments contain an inner layer and outer layer. The inner layer has the characteristic of being liquid permeable so as to allow the body fluids to flow into it and be absorbed. The outer layer has the characteristic of being liquid impermeable but air permeable, so that the liquid absorbed in the inner layer does not strike through the outer layer. The breathability of the outer layer also reduces wet feeling and will in fact allow some evaporation of liquid collected in the inner layer. An example of such two layer undergarments is provided by way of Applicant's Canadian Patent No. 2,149,477, issued Apr. 8, 1997 and its pending U.S. patent application Ser. No. 08/971, 327 filed Nov. 17, 1997, the disclosures of which are hereby incorporated by reference in their entirety. In general, these documents describe a garment in the form of an undergarment or an outerwear which has a body conforming lower torso portion for preventing leakage of body waste liquids. The torso portion is formed of sheet material which at least in the crotch portion consists of a liquid permeable inner layer and a juxtaposed outer layer which is breathable but liquid impermeable. Bodily fluids which come into contact with the liquid permeable inner layer pass into or are absorbed by the inner layer and which fluids subsequently come into contact with the outer layer. Since the outer layer is vapour permeable but liquid impermeable, the liquid which has been held inwardly of the inner layer (and away from the wearer's skin) is permitted to evaporate to a certain extent.

To increase the capacity of absorbency, it is known to insert an absorbent layer inserted in between the inner and outer layers. A reusable brief from Roche Product. Limited [Medical Textiles January, p 3, 1994; Medical Textiles January, p 3, 1993] is an example of three layer undergarment, which has a cut away high leg shape and lace trim for an active lifestyle. It contains a rounded insert made from the special absorbent KYLIE™ for providing an effective absorbency of 50-75 milliliters per gram absorbent. However, three-layer systems not only require an additional constituent, but also involve a more complex manufacturing process.

For those products which need more comfort and which are not necessarily of great absorbency, two layer undergarments are proposed by different studies. C. L. Weimer [Medical Textiles December, p 9-10, 1997] described an undergarment made of polyurethane coated nylon with moderate absorbency. U.S. Pat. No. 5,300,053 dated Nov. 4, 1991 to D. M. Genaro describes a two layer brief with a liquid impervious layer and a liquid pervious layer. However, the composition of two layers was not specified.

In early days, the outer layer was typically made from polyethylene [U.S. Pat. No. 5,520,673 dated May 28, 1996 to Menasha et al], polypropylene [U.S. Pat. No. 4,518,451 dated Sep. 2, 1982 to T. J. Luceri] or polyvinylchloride (PVC). These materials are liquid impervious as well as air impermeable. Nowadays, air permeable but liquid impervious materials are used more and more, such as a polyurethane coated knitted polyester [U.S. Pat. No. 4,352,356 dated Oct. 5, 1982 to D. P. Tong] or a polyurethane coated non-woven as a liquid impervious panel for urinary incontinence garment [U.S. Pat. No. 5,085,653 Feb. 4, 1992 to H. Levy; Anonymous Vliesstoff Nonwovens International No. 5, p 163, 198, 1989]. Kuner Textilwerke GmbH [Anonymous, Techtex Forum No. 7-8, p 184, 1993] developed a new medical fluid barrier named Humiditex™ which is a polyurethane based membrane. It can be used in conjunction with all types of textile materials and served as operating apparel, bedsheets, incontinence products, diapers and underwear. Gore-Tex™ is a porous membrane made of polytetrafluoroethylene (PTFE). It has good air and moisture vapour permeability but it is liquid impervious. To economize the products, other kind of porous membranes are used to replace Gore-Tex™. ECTFE (polyethylene-chlorotrifluoroethylene) [Ausimont Halar ECTFE Fluoropolymer Guide USA 1997] membrane has excellent moisture vapour permeability as well as high tensile strength, elongation and flexibility.

To obtain high efficiency of reusable absorbent, some interesting materials have been developed. U.S. Pat. No. 5,360, 421 dated Aug. 16, 1993 to D. W. Revelle describes an absorbent textile garment with bicomponent textile liner. The liner next to wearer's skin is a knitted bicomponent textile to provide a material having a nylon face and an opposite polyester face. The hydrophilic nylon is a copolymer of nylon 6 and polyethylene oxide diamine (product Hydrofil™ of Allied Signal Inc.). The moisture or the liquid is transferred from polyester side to nylon side. So that the liner has the function of both absorbing and maintaining a high degree of comfort for the wearer even after it has been wetted. Some modified polymers can be used as a super absorbent. A fabric capable of absorbing large amounts of water is produced by the basic hydrolysis of polyacrylonitrile fibers [U.S. Pat. No. 4,337,328, 1982 to Holst et al]. U.S. Pat. No. 4,411,660 dated Apr. 14, 1982 to F. S. Dawn] describes a super absorbent with high molecular weight acrylic polymer containing hydrophilic carboxylate groups. However, the polymer forms a gel on contacting with aqueous solutions. An absorbent comprising of a blend of antimicrobial acrylic fibers and hydrophilic cellulosic fibers is taught in U.S. Pat. No. 5,562,648 dated Mar. 31, 1995 to R. H. Peterson. In Peterson's U.S. Pat. No. 5,350,625 dated Jul. 9, 1993, he mentions that 35/65 acrylic/rayon fabric has a good absorbency as well as a good retention. Phosphorylated or acrylamide grafted cellulose has an ability of ion-exchange [M. Weltrowski and R. Toupin Fabric Formation 1996 pp 71-75], which can be used to remove the odours of urine [Japan JP 62,237,924 dated Oct. 17, 1987 to H. Simizu; Japan JP 62,298,359 Jun. 18, 1986 to T. Fujii] and maintain the desirable acidic pH to control the infection and inflammation in women's underwear [V. G. Zaikov Polymer Degradation and Stability No. 36, 1992 pp 49-52].

Some patents are related to design of the absorbent undergarments. An ingenious design can impart good qualities to the underwear. Stretchable openings at waist and legs are described in U.S. Pat. No. 5,683,374 dated Apr. 23, 1996 to M. Yamamoto; and U.S. Pat. No. 4,847,134 dated Dec. 22, 1987 to A. M. Fahrenkrug; or guards at the side of the pads [Anonymous, Nikkei Weekly No. 1688:20, P 33, September 1995] prevent leakage.

With all this activity and the potential for such products, the market has yet to experience a material or a product which is genuinely reusable and which is not evident that it is a product designed for such purposes. As indicated above, the thickness alone in many prior art attempts gives an institutional or "adult diaper" appearance and the level of comfort is much to be desired.

There is, therefore, a need for a liquid impermeable fabric material Mich permits the absorption and retention of minor volumes of liquids while the liquid is allowed to evaporate.

Further, there is a need for such a material from which articles can be manufactured which have effectively the same appearance and level of comfort as the articles they intend to replace, yet provide functional features not available with such articles.

There is also the need for a material from which garments, undergarments, outerwear, swimwear, active wear, and work wear can readily be assembled without the need for specialized equipment and which material is capable of absorbing or drawing a bodily fluids away from the wearer's skin for evaporation without penetration of the fluid through the entire thickness of the material. Furthermore, there is a need for such a material which closely conforms to typical materials in wearability and washability. There exists the need for such a material which can be used as the fabric for the garments themselves or as a functional lining in such garments.

There is further a need for a reusable (i.e. launderable) material which can be incorporated into garments for discretely dealing with minor bodily fluid emissions and which functions to prevent embarrassing situations or to alleviate issues of self-consciousness when worn. Such a material should be stain resistant. More specifically, there is the need for a material which can be fashioned into hygienic undergarments which are virtually indistinguishable from normal undergarments in comfort, wearability, durability, and style. Such a hygienic undergarment and should be capable of preventing leakage from body fluid flows which are not necessarily of great quantity and may be worn either in combination with existing protective products or alone. It is also desirable to provide comfort while not being conspicuous.

SUMMARY OF THE INVENTION

Accordingly, there is provided a launderable/reusable, leak-proof, breathable fabric and, more specifically, a composite fabric comprised of a liquid absorptive layer and a liquid impervious but vapour permeable layer. Such fabric is useful in drawing fluids away from a source and retaining them within the absorptive layer while evaporation thereof takes place though the vapour permeable layer.

This material consists of two juxtaposed layers. The inner layer has the characteristic of being liquid permeable so as to allow the body fluids to flow into it and be absorbed. The outer layer has the characteristic of being liquid impermeable but air or vapour permeable, so that the liquid absorbed in the inner layer does not strike through the outer layer. Because the body fluids can flow into the inner layer, the wearer does not experience a clammy feeling from the material next to the skin. The breathability of the outer layer also reduces wet feeling and will in fact allow some evaporation of liquid collected in the inner layer. Because the fluid is drawn away from the body, the possibility of skin irritation is reduced.

A material has been developed which provides the functions of absorbing or drawing minor quantities of bodily fluids away from the wearer yet is sufficiently thin and comfortable to be inconspicuous. In addition, the resulting fabric material is capable of being laundered and substantially retains its properties after numerous cycles of use and washing.

Broadly stated, the material according to the invention is fabricated from an absorbent acetate fiber based fabric to which is laminated or adhered a liquid imperviousness but vapour permeable polyurethane film, to result in an substantially integral fabric material from which articles can be manufactured which can take advantage of the material's absorbent, launderable/reusable, leak-proof and breathable nature.

More specifically, there is provided in one aspect of the invention a composite fabric material comprising an absorbent first layer to which is adhered a vapour permeable and liquid impervious second layer, said first layer comprising a fabric comprising acetate fibers, and said second layer comprising microporous polyurethane. There is also provided an article for absorption and evaporation of bodily fluids made at least in part from this composite fabric material.

In another aspect of the invention, there is provided a composite fabric material for use in articles of manufacture for absorbing fluids and retaining them while they are permitted to be evaporated at least in part, said material comprising an absorbent first layer to which is adhered a vapour permeable and liquid impervious second layer, said first layer comprising a fabric comprising acetate fibers, and said second layer comprising microporous polyurethane, said first layer being contactable with the bodily fluid for absorption thereof and retention therein while said second layer permits evaporation of the absorbed and retained bodily fluid.

There is also provided a fabric material comprising an absorbent first layer to which is adhered a vapour permeable and liquid impervious second layer, characterized in that said material has a liquid absorption capacity of between about 3 and 9 g per g of material, a liquid retention capacity under a 100 g centrifugal force of between about 0.32 and 0.35 g per g of material, and a thickness of between about 0.6 and 1.4 mm.

Furthermore, in accordance with another aspect of the invention, there is provided a composite fabric material comprising an absorbent first layer to which is adhered a vapour permeable and liquid impervious second layer, said first layer comprising a fabric comprising acetate fibers, said first layer being brushed on one side thereof and wherein said second layer is juxtaposed said brushed side of said first layer.

While the primary purpose for such a composite fabric is initially seen as the primary component (as a gusset, an insert or the fabric of manufacture) for underwear, either female panties or male briefs, undergarments for children in the latter stages of toilet training, as outerwear such as athletic tights and bathing suits; as inserts for nursing brassieres or the material of the nursing bra itself, etc., it is also envisaged that such a material could be employed in bedding, in whole or in part, as absorbent, breathable inserts in various garments, and in specialty applications such as clothing in the medical field as mentioned above. The composite fabric material could find application in various products, either in whole or in part, to permit bodily fluids, liquids or other flowable matter, to be absorbed, but not transmitted through the material, except perhaps, in vapour form, and further where it is desirous to have a washable and, hence, reusable article which is stain resistant and exhibits a certain degree of comfort. In this regard, the material could be used as a covering material on articles, if on which anything is spilled, can simply be removed, laundered and redeployed. The material may also find use as a reusable applicator for products which might cause irritation to the skin (but which are not detrimental to the fabric constituents), where the product is retainable on the absorbent side while the hand need only contact the liquid impervious side.

The composite fabric may be used alone or in combination with one or more layers of other breathable materials or fabrics, where such material is disposed on the liquid impervious side so as not to prevent evaporation, or one or more layers of liquid permeable materials or fabrics, where such material is on the absorbent side so as to enable liquid to be contactable with the absorbent side. The subject material may be attached to these other materials at seams, for example as a gusset panel in underwear, or attached, affixed, adhered in other manners which are not detrimental to the subject material's functionality. The subject material may also be combined (laminated or otherwise) to a second absorbent layer so as to sandwich the liquid impervious layer to provide a bi-directionally functional material.

These and other features and advantages will become more apparent from the detailed description hereinbelow along with the attached drawings.

DETAILED DESCRIPTION OF THE INVENTION

Selection of Materials

It would appear difficult if not impossible to derive a single (layer) material which was capable of absorbing or drawing bodily fluids away from the body for temporary retention until they evaporate at least in part, yet ensure the material was liquid impervious. However, a composite material could provide the necessary functions by way of individual functional layers and yet be manufactured in such a manner so as to be highly similar to a single layer material in look, feel, comfort, and wearability, and in its ability to be rendered into garments, liners for garments, bedding, etc., in much the same way as single layer fabrics using known manufacturing techniques.

Based on the information obtained from research into these problems and knowledge of various fabrics and textiles, the following six materials were proposed, which from theoretical considerations would be suspected of having moderate absorbency and a dry and comfortable feeling when worn:

(1) 35/65 acrylic/rayon knitted fabric inner layer (~150 g/m$^2$≈4.4 oz/yd$^2$) with a polyurethane outer layer,
(2) 50/50 polyester/cotton knitted fabric inner layer (~150 g/m$^2$) coated with polyurethane;
(3) 100% hydrophilic nylon 6 (product Hydrofil of Allied Signal Inc.) knitted fabric inner layer (~150 g/m$^2$) coated with polyurethane;
(4) bicomponent: polyester and rayon two face knitted fabric with a polyurethane layer on the rayon surface;
(5) 65/35 polyester/rayon knitted fabric inner layer (~150 g/m$^2$) with a polyurethane outer layer, and
(6) 100% cotton knitted fabric inner layer with a polyurethane outer layer.

When the term "inner" and "outer" are used herein, relativity is dictated by proximity to the wearer's skin. Thus, in a material used for bedding, the inner layer would be the (upper) layer on which the user rests whereas the "outer" layer would be the (lower) layer adjacent the mattress.

The liquid impervious, vapour permeable layer is suggested to be in the form of a film or membrane which can be attached, affixed or otherwise adhered to the absorbent layer. This layer can be either hydrophillic or microporous polyurethane which are essentially water insoluble to be capable of withstanding numerous washings.

Testing Protocol
Standard Methods

Testing experiments utilized in the development of this fabric material are based on the standard test methods which are listed in Table 1, unless otherwise specified.

TABLE 1

Standard Methods for Testing

| Test | Properties | Standard Test Method |
|---|---|---|
| (1) | Weight (unit mass of fabric) | CAN/CGSB[1] - 4.2, 5.1 |
| (2) | Thickness | CAN/CGSB - 4.2, 37 |
| (3) | Composition | CAN/CGSB - 4.2, 14.1 to 14.18 |
| (4) | Puncture resistance | TP 1342 (F) |
| (5) | Pilling resistance | CAN/CGSB - 4.2, 51.2 (random tumble paling tester) |
| (6) | Absorption and retention capacity of artificial blood and urine | INDA[2] 10.1 & ASTM[3] D2402-90 (centrifugal force 100 g) |
| (7) | Wicking rate | INDA 10.1 |
| (8) | Resistance to penetration of artificial blood and urine | ASTM F903 (procedure B: 0 psi for 5 min followed by 1 psi for 10 min) |

TABLE 1-continued

Standard Methods for Testing

| Test | Properties | Standard Test Method |
|---|---|---|
| (9) | Stretch and reset | ASTM 2594 |
| (10) | Moisture vapor transmission | CAN/CGSB - 4.2, 49 AATCC[4] 130-1990 (oily stain release method) |
| (11) | Stain release of artificial blood | |
| (12) | Wash durability - Domestic laundering | CAN/CGSB - 4.2, 58 |

NOTES:
[1]Canada/Canadian General Standard Board
[2]Association of the Nonwoven Fabric Industry
[3]American Society for Testing and Materials
[4]American Society of Textile Chemists and Colorists

Washing Procedure

In order to observe the effect of washing on the physical properties (dimensional change, moisture vapor transmission) and absorbent properties (wicking rate, absorbency and retention under pressure), the samples were washed with non-ionic detergent at 40° C. for 50 times. All the samples after washing and drying were conditioned at RH 65% and 21±1° C. at least 24 hours.

Synthetic Urine and Synthetic Blood

Synthetic urine and synthetic blood used in the experiments were prepared as follows. Synthetic urine as suggested in U.S. Pat. No. 5,331,021 dated Jul. 19, 1994 to Ahmed et al, contains 0.64 g $CaCl_2$; 1.14 g $MgSO_4.7H_2O$; 8.20 g NaCl; and 20.0 g urea dissolved in 1000 g deionized water. Synthetic blood as indicated by ASTM Test Method F23.40.05, is prepared by dissolving 25.0 g thickening agent (Acrysol G110™) and 10.0 g Direct Red 81 in quality distilled water (pH 7.0±0.5) then being adjusted to a surface tension 42±2 dyne/cm. Acrysol G110™ and Direct Red 81™ were purchased from Johnson Moen Co. (USA). Quality distilled water was from BDH Inc. for high performance liquid chromatography. It was found that the artificial blood has a higher absorption and retention on the materials than artificial urine and water. This could be because its surface tension ($\sigma$=42 dyne/cm) is lower than that for artificial urine ($\sigma$=73 dyne/cm) and water ($\sigma$=73 dyne/cm), but its viscosity ($\eta$=16 cps) is higher than artificial urine ($\eta$=0.94 cp) and water ($\eta$=1.0 cp).

Material Collection and Preliminary Evaluation

A number of companies who produce knitted fabrics were canvassed to obtain samples of fabrics of having roughly the same constituents as the materials which held promise from the aforementioned research. Sixteen samples were acquired and these are specified in Table 2.

TABLE 2

Collected materials and manufacturers

| Code | Fiber content | Mass (g/m$^2$) | Manufacturer | Manufacturer's Ref. |
|---|---|---|---|---|
| A | 100% cotton | 158 | Stanfield's Limited | |
| B | 87/13 poly[1]/cotton | 141 | Unknown | |
| C | 65/35 poly/cotton | 150 | Agmont Inc. | Piece No. 8333429 |
| D | 65/35 poly/cotton | 152 | Les Tissus A & G (1982) Inc. | Interlock Style CP456(c)/K |
| E | 50/50 poly/cotton | 120 | Château Lingerie | |
| F | 50/50 poly/cotton | 140 | Château Lingerie | |
| G | 100% Coolmax[2] | 120 | Tricots Daveluy Inc. | Jersey Style JE-5000 |
| H | 50/50 poly/Coolmax | 110 | Tricots Daveluy Inc. | Jersey Style JE-5010B |

TABLE 2-continued

Collected materials and manufacturers

| Code | Fiber content | Mass (g/m²) | Manufacturer | Manufacturer's Ref. |
|---|---|---|---|---|
| I | 50/50 cotton/Coolmax | 110 | Tricots Daveluy Inc. | Jersey Style JE-5020P |
| J | 50/50 poly/Cotton | 100 | Tricots Daveluy Inc. | Jersey Style JE-3293P |
| K | 97/3 poly/Lycra[3] | 160 | Tricots Daveluy Inc. | Jersey Style JL-4660B |
| L | poly/viscose/Lycra | 225 | Idole Collections | |
| M | 100% acrylic | 135 | Testfabric | #867 |
| N | 53/47 poly/acetate (suede)[4] | 90 | Milco Industries Inc. | Style 9463 |
| O | 60/40 poly/Hydrofil[5] nylon (suede)[4] | 80 | Milco Industries Inc. | Style 6500 |
| P | 80/20 acetate/nylon[6] (suede)[4] | 70 | Milco Industries Inc. | Style 9465 |

NOTES:
[1] Polyester
[2] Coolmax ™ of E. I. du Pont De Nemours and Company consists of non-circular cross-section polyester fibers
[3] Lycra ™ of E. I. du Pont De Nemours and Company (spandex) - consists of polyurethane fibers.
[4] Suede = brushed/napped
[5] Hydrofil ™ of Allied Signal Inc. consists of hydrophillic nylon 6 fibers
[6] Made with Microsafe ™ (Hoechst Celanese Corporation) cellulose acetate (diacetate) fibers.

It is considered important that the material should possess relatively high absorption properties yet be relatively low in retention. This combination of properties gives rises to materials which, when used next to the wearers skin, provides a dry feeling. To screen (i.e. eliminate) less than desirable materials and to reduce the overall amount of testing required, the water absorption and retention capacity of the collected fabrics were evaluated. The results, which form the basis of the initial selection criteria, are shown in Table 3.

TABLE 3

Absorption and retention capacity of the collected materials

| Code | Mass (g/m²) | Absorption capacity (g/g fabric) | Retention capacity (Centrifugal force 100 g) (g/g fabric) |
|---|---|---|---|
| A | 158 | 2.9 | 1.26 |
| B | 141 | 2.55 | 0.43 |
| C | 150 | 3.21 | 0.76 |
| D | 152 | 3.23 | 0.58 |
| E | 120 | 2.89 | 0.75 |
| F | 140 | 2.48 | 0.83 |
| G | 120 | 2.77 | 0.57 |
| H | 110 | 2.45 | 0.44 |
| I | 110 | 3.32 | 1.02 |
| J | 100 | 3.48 | 0.75 |
| K | 160 | 3.20 | 0.41 |
| L | 225 | 2.44 | 0.73 |
| M | 135 | 2.45 | 0.57 |
| N | 90 | 1.76 | 0.30 |
| O | 80 | 3.77 | 0.44 |
| P | 70 | 6.53 | 0.41 |

From Table 3, it can be seen that cotton has high absorption and retention, while polyester has low absorption and retention. Because Coolmax™ is a polyester fiber with triangle cross section, it has nearly the same absorption as polyester but higher retention than polyester fibers (compare materials H and J). It is interesting to note that the fabric of polyester containing Lycra™ (material K) has high absorption but is low in retention. However, viscose (material L) does not have a high absorption as was expected from the aforementioned research. Acrylic fabric (material M) does not have a very high absorption either.

As expected, Hydrofil™ nylon has high absorption and low retention (material O). The acetate/nylon (material P) also has extremely high absorption and low retention. The suede/brush treatment is believed to further increase the absorbency. The un-brushed side, intended to be worn adjacent the skin, lets wearer feel dry which is considered to be a desirable property. This arrangement lets the material have a property like a bicomponent fabric as mentioned above from library research.

Figure 1:
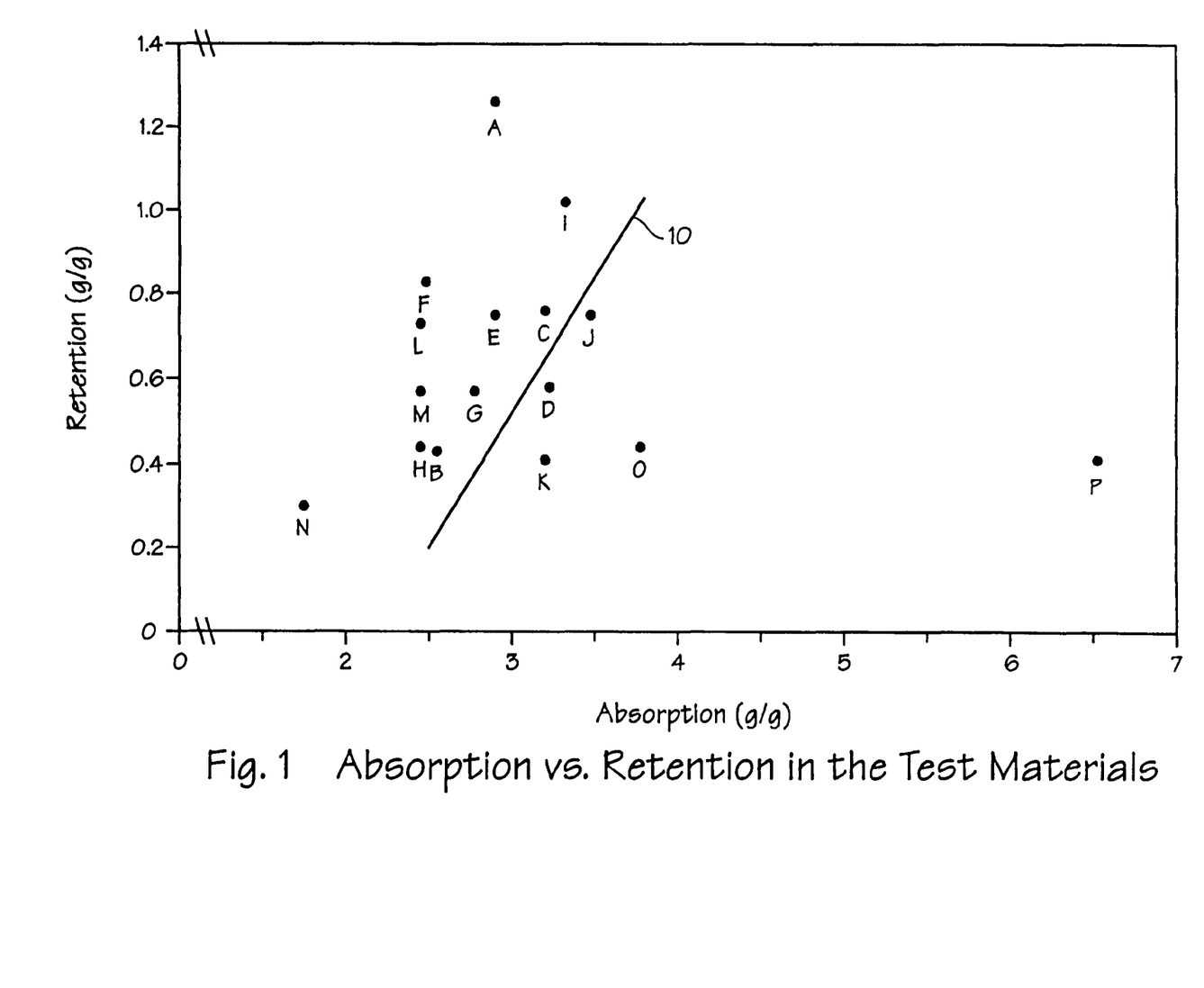
FIG. 1 is a chart of the absorption vs. retention properties of the test materials which is used to set initial selection criteria for the absorbent layer of the fabric material.

To facilitate comparison of the tested materials, FIG. 1 shows the relationship between the absorption and retention of each of the sixteen test fabrics.

Based on the criteria of selection mentioned above, the materials in the lower right in FIG. 1 should be chosen, which have higher absorption and lower retention. A generally arbitrary line 10 was drawn to obtain the five best selections based on the aforementioned criteria, namely: materials D; J; K; 0; and P. The results are summarized in Table 4.

TABLE 4

Preliminary selected five materials

| Code | Fiber content | Mass (g/m²) | Absorption capacity (g/g fabric) | Retention (Centrifugal force 100 g) (g/g fabric) | Manufacturer |
|---|---|---|---|---|---|
| D | 65/35 poly/cotton | 152 | 3.23 | 0.58 | Les Tissus A & G (1982) Inc. |
| J | 50/50 poly/cotton | 100 | 3.48 | 0.75 | Tricots Daveluy Inc. |
| K | 97/3 poly/lycra | 160 | 3.20 | 0.41 | Tricots Daveluy Inc. |
| O | 60/40 poly/Hydrofil nylon (suede) | 80 | 3.77 | 0.44 | Milco Industries Inc. |
| P | 80/20 acetate/nylon (suede) | 70 | 6.53 | 0.41 | Milco Industries Inc. |

Tests on the Coated Fabrics Before Washing

Figure 2:
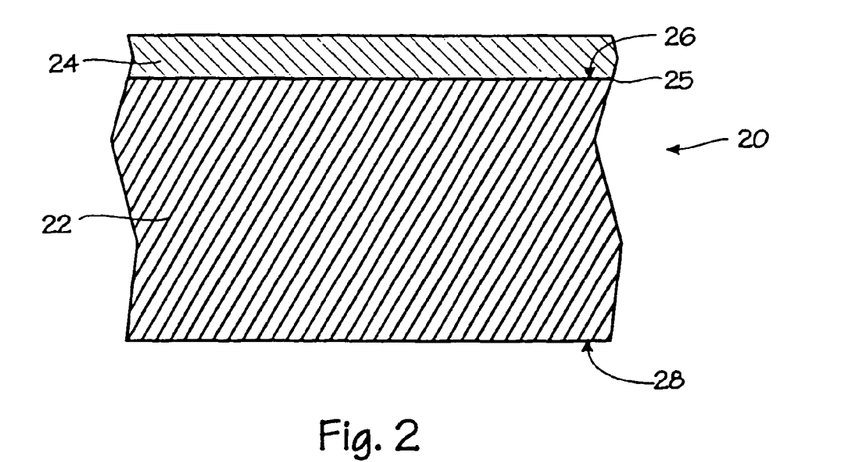
FIG. 2 is a schematic drawing of the general form of the fabric material in accordance with the invention.

Now that reasonable prospects for the absorbent layer were selected, marriage with the prospective liquid-impervious/vapour-permeable layer or functional equivalent is necessitated. To this end, a film or membrane which is laminated with the absorbent layer is preferred over a coating or impregnation as it is easier to control the process to ensure the entirety of the resultant material is liquid-impervious and vapour-permeable because of the integrity of the film or membrane. FIG. 2 shows a representation of the resulting material 20 which is comprised of an absorbent layer 22 which is intended to be positioned proximal or adjacent the wearer's skin is juxtaposed with a distal liquid-impervious/vapour-permeable layer 24. The absorbent layer 22 absorbs or draws bodily fluid away from the wearer. The liquid-impervious/vapour-permeable layer 24 prevents the retained bodily fluid from being transmitted through the entirety of the thickness of the material 20. However, evaporation of the bodily fluid can occur.

As indicated above, two types of liquid-impervious/vapour-permeable films were contemplated as being potentially useful: (1) hydrophilic polyurethane film and (2) a microporous polyurethane film. These film reference numerals are used to identify the resulting laminated fabric material in conjunction with the absorbent fabric code, i.e. D1 and D2. In general, hydrophillic polyurethane is comprised of polymeric chains that enable reversible hydrogene links with water molecules in order to allow moisture vapour transmission. Microporous polyurethane includes interconnected pores that vary in size from 0.1 to 10 microns which is sufficient to permit passage of water molecules (water vapour) but not water in liquid form.

The two layers 22,24 have to be attached, affixed or otherwise adhered sufficiently to one another in such a manner so as to prevent delamination, particularly upon repeated cycles of use and laundering, but also in such a manner as not to detract significantly from the properties of the individual layers 22,24 or their potential cumulative effect. The films 24 were laminated to the selected absorbent materials by means of a water insoluble adhesive 25. More specifically, a polyurethane-based adhesive was applied in a discontinuous manner (i.e. by spraying) to effect a network of spaced apart adhesion points. In general, a variety of methods for effecting lamination are known in the industry. Three such methods are described below.

(1) Rotary Gravure roll—A steel roll engraved with a pattern (it can be lines or dots) turns into an adhesive solution to pick up the adhesive in a discontinuous fashion. The roll once saturated with the adhesive is pressed onto the tricot/fabric. The film is applied onto the tricot carrying the adhesive. The laminate in then taken into a drying and/or curing stage.

(2) Rotary screen—Screen, or perforated steel plates, are put in roller forms. Adhesive is pumped into the roller and forced out of the screen. Using this technique, the tricot/fabric is passed under the rotary screen to be coated with adhesive in a discontinuous pattern. The film is then combined to the tricot/fabric. The laminate in then taken into a drying and/or curing stage.

Figure 3:
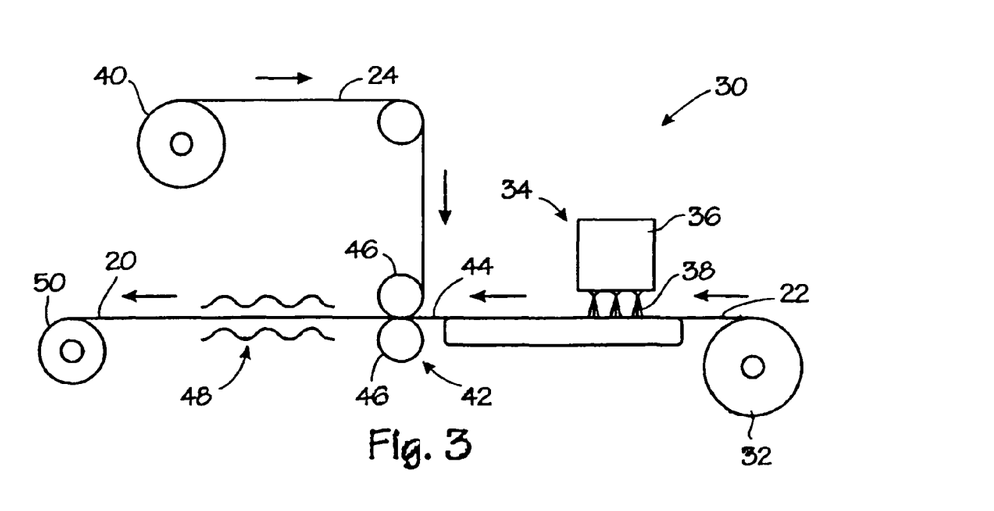
FIG. 3 is a schematic showing a typical method for manufacturing the fabric material of the present invention.

(3) Spray application—The tricot/fabric is passed under adhesive sprayers that will apply a layer of adhesive in a discontinuous pattern. The film is then combined to the fabric. The laminate in then taken into a drying and/or curing stage. FIG. 3 illustrates this process schematically. The laminating apparatus is shown generally at 30. A fabric roll 32 dispenses fabric 22 to a spray area 34 where a sprayer 36 sprays adhesive 38 onto the fabric 22. A film roll 40 dispenses film 24 to press area 42 where the film 24 is pressed onto the adhesive bearing fabric 44 as they travel through press rollers 46. The resulting material 20 is then taken through the drying and/or curing zone 48 and subsequently wound on take-up roll 50.

In method (1) the adhesive can be solvent based or water based. In method (2) and (3) the adhesive can be solvent based, water based or "hot melt" which is 100% solid and must be heated in order to become sufficiently liquid to be applied appropriately.

The five selected materials of Table 4 were laminated using method (3) with 30 micron thick hydrophilic and microporous polyurethane layers.

After laminating, it was found that K1 and K2 curled significantly, especially K2. This could present serious difficulties for garment making.

Physical properties, weight, thickness, resistance to puncture, to pilling, stretch and reset and moisture vapor transmission of the 10 resulting materials were tested and the results were listed in Table 5.

TABLE 5

Characteristics of the selected materials after laminating

| Code | Fiber content | weight (g/m²) | Thickness (mm) | Puncture (N) | Pilling[1] after 30 min | Stretch/reset % (elongation after 1 hour) wale | course | Moisture vapor transmission (mm) |
|---|---|---|---|---|---|---|---|---|
| D1 | 65/35 poly/cotton | 204.9 | 0.71 | 161.5 | 1.0 | 1.2 | 3.9 | 10.0 |
| J1 | 50/50 poly/cotton | 136.4 | 0.46 | 136.1 | 4.0 | 0.8 | 4.5 | 10 |
| K1 | 97/3 poly/lycra | 199.2 | 0.72 | 192.7 | 1.5 | 1.6 | 3.5 | 10 |
| O1 | 60/40 poly/Hydrofil ™ nylon (suede) | 108.4 | 0.34 | 113.4 | 5 | 0.8 | 10.2 | 13 |
| P1 | 80/20 acetate/nylon (suede) | 110.6 | 0.65 | 47.8 | 5 | 0.4 | 9.8 | 8.6 |
| D2 | 65/35 poly/cotton | 200.2 | 0.7 | 191.5 | 1 | 2.4 | 7.5 | 5.8 |
| J2 | 50/50 poly/cotton | 135 | 0.47 | 144.4 | 4.5 | 2 | 9.1 | 5.8 |
| K2 | 97/3 poly/lycra | 198.5 | 0.72 | 186.5 | 2.5 | 2.8 | 4.3 | 6 |
| O2 | 60/40 poly/Hydrofil ™ nylon (suede) | 112.1 | 0.65 | 115.4 | 5 | 2.8 | 10.2 | 4.6 |
| P2 | 80/20 acetate/nylon (suede) | 104.9 | 0.63 | 51.5 | 5 | 2 | 8.7 | 6.5 |

NOTES:
Pilling[1]: Grade 5 = no pilling; Grade 1 = serious pilling.

The absorption properties of the laminated fabrics were measured and the results are shown in Table 6.

TABLE 6

Absorption and retention capacity of the selected materials (laminated)

| Code | Fiber content | Absorption capacity (g/g fabric) | Retention capacity (Centrifugal force 100 g) (g/g fabric) | Wicking rate (mm/5 min) WD[1] | CD[1] |
|---|---|---|---|---|---|
| D1 | 65/35 poly/cotton | 2.61 | 0.53 | 62 | 56 |
| J1 | 50/50 poly/cotton | 2.42 | 0.66 | 7 | 12 |
| K1 | 97/3 poly/lycra | 2.51 | 0.44 | 28 | 25 |
| O1 | 60/40 poly/Hydrofil nylon (suede) | 1.99 | 0.42 | 19 | 19 |
| P1 | 80/20 acetate/nylon (suede) | 4.77 | 0.45 | 31 | 29 |
| D2 | 65/35 poly/cotton | 2.74 | 0.48 | 69 | 67 |
| J2 | 50/50 poly/cotton | 2.3 | 0.53 | 19 | 16 |
| K2 | 97/3 poly/lycra | 2.35 | 0.44 | 48 | 58 |
| O2 | 60/40 poly/Hydrofil nylon (suede) | 1.87 | 0.35 | 35 | 29 |

TABLE 6-continued

Absorption and retention capacity of the selected materials (laminated)

| Code | Fiber content | Absorption capacity (g/g fabric) | Retention capacity (Centrifugal force 100 g) (g/g fabric) | Wicking rate (mm/5 min) WD[1] | CD[1] |
|---|---|---|---|---|---|
| P2 | 80/20 acetate/nylon (suede) | 3.82 | 0.33 | 33 | 43 |

NOTES:
[1]WD: Wale direction, CD: Course direction

Comparing Table 6 with Table 4, it can be seen that after laminating, absorption and retention capacities decreased and the fabrics with coating layer 2 have less absorption. Table 6 shows that among the five selected materials after coating, material P has the highest absorption capacity and the lowest retention capacity, which is good for the wearer to feel dry if there is any body fluid occurs. Material P also has a moderate wicking rate which is important to the wearer. If the wicking rate is too high, the body fluid is easy to spread everywhere and to the edge of the underwear and special attention at the seams may be necessary. However, if the wicking rate is too low, the body fluid rests on the inner surface of the fabric for a relatively long time. This could be uncomfortable to the wearer.

Table 7 tabulates the results of resistance to penetration and to stain of the selected laminated materials.

TABLE 7

Resistance to penetration and to stain of the selected materials (laminated)

| Code | Resistance to penetration of artificial urine and artificial blood[1] | | | Stain release - of artificial blood (gray scale) |
|---|---|---|---|---|
| | Drop test | 0 psi 5 min | 1 psi 10 min | |
| D1 | penetration | 2 | 2 | Grade 2-3[3] |
| J1 | penetration | 2 | 2 | Grade 1 |
| K1 | penetration | 2 | 2 | Grade 4-5 |
| O1 | penetration | 2 | 2 | Grade 1-2 |
| P1 | penetration | 2 | 2 | Grade 3-4 |
| D2 | no penetration | no penetration | no penetration | Grade 3 |
| J2 | no penetration | no penetration | no penetration | Grade 1 |
| K2 | no penetration | no penetration | no penetration | Grade 4-5 |
| O2 | no penetration | no penetration | no penetration | Grade 2 |
| P2 | no penetration | no penetration | no penetration | Grade 5 |

NOTES:
[1]the results on artificial urine are the same as that for the blood;
[2]not necessary to continue the test due to penetration in drop test;
[3]Grade 5 no stain after washing; Grade 1 serious stain after washing.

Table 7 shows that the resistance to penetration depends on the laminating layer rather than on the fabrics. The laminating layer 2 (microporous) has good resistance to penetration of artificial urine and blood, but the laminating layer 1 (hydrophilic) has no resistance to them. At the same time, laminating layer 2 has better moisture vapor transmission than laminating layer 1 (see Table 5), so that it is found that laminating layer 2 is generally better than laminating layer 1 on the selected five fabrics to result in a wash-durable, leak-proof and breathable fabric.

From Table 7, it can be seen that the laminating layer also affects the stain release of artificial blood after washing, even though the blood was stained on the fabric side. The fabric with laminating layer 2 has better stain release than that with laminating layer 1 except with J1, J2. Material J had the most serious stain among the 10 samples after washing. K1, K2 have good release of stain after washing. However, as it is mentioned above, material K curled significantly after laminating and even more so after washing. This is unacceptable for purposes of a fabric from which garments or bedding and the like are made. Lastly, it can be seen that P2 has no blood stain after washing.

Based on the testing results, it can be seen that P2 has the highest absorption capacity and the lowest retention capacity among the selected materials, which is good for the wearer to feel dry if any body fluid emission occurs. P2 also has a moderate wicking rate and moisture vapor transmission which are also important to the wearer. Besides, P2 has good resistance to pilling, penetration and staining. When the resistance to puncture is not the first consideration, which it will not be in many of the aforementioned potential applications, P2 certainly outperforms the other materials. The acetate/nylon fibers of material P are capable of made with built-in anti-microbial protection that does not wash out under normal washing conditions. Since the fibers themselves are anti-microbial, bacteria based odours can be reduced.

Wash Durability

To test the wash durability of the selected materials, the samples were washed by the standard method CAN/CGSB 4.2 No. 58 M90 in a washing machine at 40° C. with 4 g/l Tide™ detergent and dried at 65-70° C. in a conventional clothes dryer. After one washing, the laminated layer of the materials shrunk a little and some creases appeared. After 50 times washing, delamination started to appear at some places on the samples, but not to a significant extent. 50 washes is considered to be in the upper range of normal life expectancy for products designed to undergo repetitive cycles of absorbing minor quantities of bodily fluids. Minor quantities of bodily fluids are considered on the order of less than about 10 g/g and typically are less than 5 g/g of material. When the term "about" is used in this description or in the claims with reference to a quantitative specification, it is intended to mean a ±5 to ±10% of the referenced value. The dimensional change of the samples after one and 50 times washing is shown in Table 8.

TABLE 8

Dimensional change of the laminated materials after washing

| | After one washing | | | After 50 washings | | |
|---|---|---|---|---|---|---|
| Code | warp | course | w + c | warp | course | w + c |
| D1 | −2.0%[1] | 1.4%[1] | 3.4% | −3.9% | −1.8% | 5.7% |
| J1 | −3.2% | −0.5% | 3.7% | −6.6% | −1.7% | 8.3% |
| K1 | −3.9% | −0.8% | 4.7% | −8.0% | −3.1% | 11.1% |
| O1 | −2.6% | 0.1% | 2.7% | −0.5% | −6.1% | 6.6% |
| P1 | −2.5% | 1.3% | 3.8% | −6.0% | −3.0% | 9.0% |
| D2 | −1.5% | 0.3% | 1.8% | −4.0% | 0% | 4.0% |
| J2 | −3.6% | −0.4% | 4.0% | −6.6% | −1.5% | 8.1% |
| K2 | −5.4% | −0.3% | 5.7% | −11.5% | −1.7% | 13.2% |
| O2 | −3.4% | −0.1% | 3.5% | −0.5% | −7.7% | 8.2% |
| P2 | −2.7% | −0.04% | 2.7% | +0.4% | −7.0% | 7.4% |

NOTES:
[1]negative means the sample shrank after washing and positive means elongation.

From Table 8, it can be seen that dimensional change after washing has not much relation with the type of laminating layer. The material D(1 and 2) have the smallest dimensional change (or highest dimensional stability) after one and 50 times washing, and the material K(1 and 2) have the second highest dimensional stability.

The physical properties of the materials after 50 time washing are listed in Table 9.

TABLE 9

Characteristics of the laminated materials after 50 washings

| Code | Fiber content | Puncture (N) | Pilling[1] after 30 min | Stretch and reset (elongation after 1 hour) wale | Stretch and reset (elongation after 1 hour) course | Moisture vapor transmission (mm) |
|---|---|---|---|---|---|---|
| D1 | 65/35 poly/cotton | 150.9 | 1 | 2.8 | 3 | 10.5 |
| J1 | 50/50 poly/cotton | 111.1 | 3 | 4.1 | 5.9 | 8.3 |
| K1 | 97/3 poly/lycra | 161.3 | 1.5 | 3.5 | 4.9 | 8.6 |
| O1 | 60/40 poly/Hydrofil nylon (suede) | 91.9 | 5 | 3.9 | 5.1 | 10.9 |
| P1 | 80/20 acetate/nylon (suede) | 49.3 | 5 | 5.5 | 4.3 | 14.7 |
| D2 | 65/35 poly/cotton | 180.3 | 1 | 4.1 | 4.1 | 5.9 |
| J2 | 50/50 poly/cotton | 119.9 | 3 | 5.1 | 5.1 | 4.6 |
| K2 | 97/3 poly/lycra | 188.9 | 1.5 | 3.9 | 5.1 | 4.5 |
| O2 | 60/40 poly/Hydrofil nylon (suede) | 102.6 | 5 | 5.1 | 7.1 | 4.8 |
| P2 | 80/20 acetate/nylon (suede) | 51.1 | 4.5 | 5.9 | 4.9 | 5.3 |

NOTES:
Pilling[1]: Grade 5 = no pilling; Grade 1 = serious pilling.

Table 9 shows that after 50 times washing, resistance to puncture decreases slightly (except P1), but the materials still have good resistance to puncture. After 50 times washing, resistance to pilling of J1, J2, K2 AND P2 decreases somewhat, while P2 has good resistance to pilling. After washing, the stretch- and reset-ability of the materials increases in wale direction and decreases in course direction. This results in a more uniform stretch and reset in two directions. Most of the materials decrease in their moisture vapor transmission capability after washing except D1 and P1, however, their moisture vapor transmission is still considered good even after washing.

The absorption properties of the materials after 50 time washing are shown in Table 10.

TABLE 10

Absorption and retention capacity of the laminated materials after 50 washings

| Code | Fiber content | Absorption capacity (g/g fabric) | Retention capacity (Centrifugal force 100 g) (g/g fabric) | Wicking rate (mm/5 min) WD[1] | Wicking rate (mm/5 min) CD[1] |
|---|---|---|---|---|---|
| D1 | 65/35 poly/cotton | 2.89 | 0.6 | 114 | 93 |
| J1 | 50/50 poly/cotton | 2.46 | 0.64 | 96 | 92 |
| K1 | 97/3 poly/lycra | 2.56 | 0.46 | 96 | 92 |
| O1 | 60/40 poly/Hydrofil nylon (suede) | 2.17 | 0.41 | 66 | 61 |
| P1 | 80/20 acetate/nylon (suede) | 3.7 | 0.47 | 56 | 55 |
| D2 | 65/35 poly/cotton | 2.72 | 0.55 | 85 | 84 |
| J2 | 50150 poly/cotton | 2.45 | 0.62 | 95 | 94 |
| K2 | 97/3 poly/lycra | 2.38 | 0.47 | 96 | 91 |
| O2 | 60/40 poly/Hydrofil nylon (suede) | 2.26 | 0.39 | 117 | 101 |
| P2 | 80/20 acetate/nylon (suede) | 3.45 | 0.53 | 66 | 63 |

NOTES:
[1]WD: Wale direction, CD: Course direction

Table 10 shows that after 50 washes, the wicking rate, absorption capacity (except that of P1, P2) and retention capacity of the materials increase. P1, P2 still have highest absorption among the materials. As mentioned above, too high a wicking rate could result in a quick spreading of the body fluids. So that P1, P2 with the lowest wicking rate after washing has the advantage of absorbing and retaining the fluids.

Table 11 shows the testing results of the resistance to penetration and to stain of the materials after 50 times washing.

TABLE 11

Resistance to penetration and to stain of the selected materials after 50 washings

| Code | Resistance to penetration of artificial urine and artificial blood[1] Drop test | Resistance to penetration of artificial urine and artificial blood[1] 0 psi 5 min | Resistance to penetration of artificial urine and artificial blood[1] 1 psi 10 min | Stain release - of artificial blood (gray scale) |
|---|---|---|---|---|
| D1 | penetration | [2] | [2] | Grade 3[3] |
| J1 | penetration | [2] | [2] | Grade 1-2 |
| K1 | penetration | [2] | [2] | Grade 4-5 |
| O1 | penetration | [2] | [2] | Grade 2 |
| P1 | penetration | [2] | [2] | Grade 4 |
| D2 | no penetration | no penetration | no penetration | Grade 3 |
| J2 | no penetration | no penetration | no penetration | Grade 1-2 |
| K2 | no penetration | no penetration | no penetration | Grade 4-5 |
| O2 | no penetration | no penetration | no penetration | Grade 2 |
| P2 | no penetration | no penetration | no penetration | Grade 4 |

NOTES:
[1]the results on artificial urine are the same as that for the blood;
[2]not necessary to continue the test;
[3]Grade 5 no stain after washing; Grade 1 serious stain after washing.

From Table 11, it can be seen that after 50 washings, the testing materials have no change of resistance to penetration. Film layer 2 keeps good resistance to penetration. Some materials such as D1, J1, O1, P1 and J2 increase resistance to staining very slightly (around half gray scale). J1, J2 have the highest resistance to staining, but they curl seriously after washing. P2 decreases the resistance to staining after washing, however, its resistance to stain is still considered good.

Testing results show that the materials after coating have good wash durability. P2 keeps excellent properties after washing.

In summary, after preliminary testing on the collected 16 samples by absorption and retention measurement, 5 fabrics were chosen. The selected 5 fabrics were coated with two different layers 1 (hydrophilic film) and 2 (microporous film). The resulting 10 materials were tested as to weight, thickness, resistance to puncture, to pilling, to penetration, to staining, stretch and reset, moisture vapor transmission, absorption and retention capacity. It is found that material P2 (80/20 acetate/nylon with film layer 2) has the highest absorption capacity and the lowest retention capacity among the selected materials, which is good for the wearer to feel dry if there is any body fluid occurs. P2 also has a moderate wicking rate and moisture vapor transmission which are also important to the wearer. Besides, P2 has good resistance to pilling, penetration and staining. P2 keeps excellent properties after 50 washes. When the resistance to puncture is not the first consideration, which it will not be in most applications, P2 is a highly practical composite fabric material for an application such as a wash-durable, leakproof and breathable undergarment.

Figure 4:
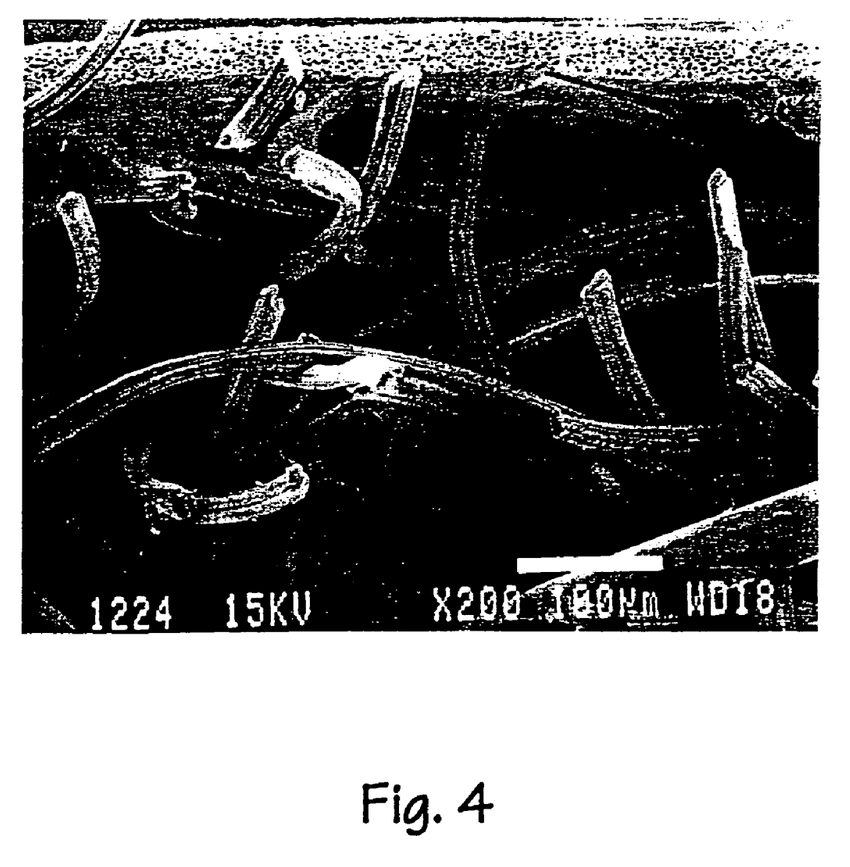
FIG. 4 is a photomicrograph showing the cross-sectional detail of the fabric material.

FIG. 4 is a photomicrograph showing a cross-sectional portion of the laminated P2 material. The (micro)porous outer layer is clearly shown near the top whereas at the upper left the predominantly acetate fibers are shown adhered to a minute dollop (on the order of 200-300 microns) of adhesive which had been applied in a discontinuous fashion leaving open areas (such as at the upper right) so as to permit vapour from fluids absorbed by the acetate/nylon layer to be evaporated through the microporous polyurethane layer. A nylon fiber is shown in the lower right corner.

More specific characteristics of the test material P are provided as follows:

| Supplier: | Milco Industries Inc. | |
|---|---|---|
| Supplier's reference: | Style 9465 | |
| Knit Type: | Warp Knit Tricot | |
| Cut (Gauge): | 32 | |
| Yarn Size | Yarn Description | Percentage (wt. %) |
| 55 D. Bright | cellulose acetate | 81% |
| 20 D. Nylon | nylon | 19% |
| Finished Width: | 60" | |
| OZ Per Square Yard: | 2.17 | |
| Wales per Inch: | 40/41 | |
| Courses Per Inch: | 41/42 | |
| Finish: | Brushed/Napped one side | |

Test material P2's vapor permeable, liquid impermeable layer is a 30 μm thick breathable microporous polyurethane membrane sold under the trademark PORELLE™. It has the following characteristics:

| Specific Weight | $15 \pm 3$ g/m$^2$ |
|---|---|
| Breaking Strength (Can/CGSB4.2M87 Method 9.1) | 13 N/50 mm |
| Elongation at Break | 200% minimum |
| Water Vapor Transmission (Can/CGSB4.2M87 Meth 49) | 4.1 mm of still air |
| Water Vapor Transfusion (ASTM E96 Precedure BW) | 3200 g/m$^2$ for 24 hrs |
| Cold Crack (ASTM D2136 @ −45° C.) | No cracking or flaking |

When knitted, the acetate/nylon fabric will have one side on which the acetate yarns are predominant while on the other side the nylon yarns will predominate. It is the side predominated by acetate yarns which is preferably brushed or napped. Brushing increases the overall thickness of the fabric layer. While it is industry standard to avoid adhering laminates to the brushed side 26 of a fabric (as the unbrushed side 28 is relatively smoother), surprisingly, better adhesion of the polyurethane film occurred when the film was laminated on the brushed side 26 of the acetate/nylon fabric. Laminating on the brushed side also provides larger open spaces on the interior of the material (i.e. between the film and the inner, non-brushed side as can be seen in FIG. 4) for both entrapment of fluids and for allowing evaporation thereof.

Acetate, as it is commonly referred to in the industry and as used herein, is actually a cellulose acetate. Acetate fibers can be cellulose diacetate or cellulose triacetate. The acetate fiber used in the knit fabric layer in test material P is cellulose diacetate. These acetate fibers may include an anti-microbial additive, such as with Hoechst Celanese Corporation's MicroSafe™ acetate fibers. The MicroSafe™ acetate fibers include 0.5-2.0% wt. % of the active anti-microbial ingredient Microban™ additive "B" from Microban Products Company of Huntersville, N.C., which is EPA registered under N. 42182-1. The anti-microbial protection contributes to a more hygienic product; inhibits the growth of odor-causing bacteria and mildew in products so that they stay fresher longer, and is engineered to last the life of the product. A built-in anti-microbial constituent is preferred over an anti-microbial coating or finish. With the former, the anti-microbial additive resides within the molecular structure of the acetate fiber and, as such, will not wash or wear off as is the tendency with post-process anti-microbial finishes or coatings.

Acetate fibers are hydrophilic and, hence, absorb water and water-based fluids. Nylon has a low water absorbency. However, they are considerable stronger so their presence in the fabric material is to provide additional strength to the resulting fabric layer. Cellulose diacetate fibers have a tenacity of about 1.2-1.5 g/denier and about the same moisture absorption as cotton. Nylon can have a tenacity of between 3 and 7 g/denier and, accordingly, by including a material such as nylon as one of the components in the knitting process in addition to acetate, the strength of the resulting fabric can be significantly increased as compared with a knit of only acetate fibers. There is, of course, a trade-off in that by increasing the amount of nylon, the strength of the resulting fabric increases, however, the amount (ratio) of absorbent acetate present in the fabric will necessarily decrease, thus resulting in a less absorbent fabric. It will be appreciated, therefore, that the optimum ratio for a given application will generally depend on the relative importance of the respective property (strength/absorbency). For example, where the composite fabric is to be used as a liner or panel where overall strength is not at issue but absorbency is important, then the content of nylon or strengthening fibers, if present, may be less than 10% by weight. In applications involving wearable garments, strength requirements are typically higher and the nylon content by weight can be 25% or more. Where undergarments with absorbency requirements are concerned, a range of about 15 to 25%, and more preferably 15 to 20% nylon has been found to provide sufficient strength without significantly compromising absorption.

As indicated above, where strength issues in the resulting composite fabric are the fabric layer can be made entirely from acetate fibers. Furthermore, since the nylon fibers play a secondary role in the fabric layer, that being mostly to provide additional strength, fibers other than nylon may be used, provided they do not adversely affect other desirable properties of the composite material. For example, polyester has been found to be an adequate substitute for the nylon. Like nylon, polyester absorbs very little water, exhibits similar strength characteristics and is aesthetically similar. Polyester can be subject to slightly greater temperatures and appears to be preferred in the medical industry over nylon.

For comparative purposes, a thicker polyester-containing acetate fabric was knit with the following characteristics:

| Knit Type: | Warp Knit Tricot | |
|---|---|---|
| Yarn Size | Yarn Description | Percentage (wt. %) |
| 55 D. Bright | cellulose acetate | 84% |
| 20 D. Polyester | polyester | 16% |
| Finish: | Brushed/Napped one side. Brushing was significant to so as to render the thickness of the fabric material to approximately ½". | |

The knitted fabric material was then laminated using method (3) above with the same 30 micron microporous polyurethane membrane sold under the trademark PORELLE™. Samples of this material were washed several times at 60° C. without any sign of delamination. Table 12 shows a comparison of the properties of this acetate/polyester fabric and the acetate/nylon test material P2.

Table 12. Comparison of properties between acetate/nylon Test material P2 and acetate/polyester fabrics with 30 micron microporous polyurethane film.

| Property | acetate/polyester | acetate/nylon |
|---|---|---|
| Specific Weight (g/m$^2$) | 129 | 104.9 |
| Thickness (mm) | 1.34 | 0.63 |
| Absorption | | |
| Artificial Blood (g/g) | 8.83 | 3.82 |
| Artificial Urine (g/g) | 0.44 | 0.33 |
| Retention | | |
| Artificial Blood (g/g) | 7.55 | 3.82 |
| Artificial Urine (g/g) | 0.32 | 0.33 |
| Wicking Rate (5 min.) | | |
| Wale Dim. (mm) | 53 | 33 |
| Course Dim. (mm) | 32 | 43 |
| Resistance to Penetration | | |
| (Drop Test/0 psi, 5 min./1 psi, 10 min.) | | |
| Artificial Blood | none/none/none | none/none/none |
| Artificial Urine | none/none/none | none/none/none |
| Water Vapor Transmission | 5.3 | 6.5 |
| (mm still air) | | |
| Stain Release of Artificial Blood | 5 | 4 |
| (Gray scale 1-5: –>5 = no stain; 1 = serious stain) | | |
| Pilling Resistance | 4-5 | 4.5 |
| (Grade 5 = none; Grade 1 = serious) | | |

As can be seen, the acetate/polyester advantageously exhibits considerably greater absorption and less retention of artificial blood and urine. While it is more than 50% thicker than the acetate/nylon, it weighs only 23% more. It has a lower wicking rate thereby better preventing spread of liquids or body fluids. The remainder of the properties are approximately on par. The greater absorption capacity is likely the result of the greater brushing and hence greater internal (i.e. between the film layer 24 and the inside 28 of the fabric layer—see FIG. 2) volume for containing liquids not absorbed by the acetate fibers.

It is contemplated that both nylon and polyester fibers can be used in conjunction with the acetate fibers to take advantage of the respective properties of each of these fibers.

It is also contemplated that the acetate fibers can be combined or knitted with one or more other fibers to form the water absorptive (permeable) layer wherein the one or more other fibers provide desired properties of those fibers to the fabric layer. As aforesaid, fibers which would adversely affect the desirable properties of the fabric layer and/or the resulting composite material when laminated should be avoided. These one or more other fibers can be included in addition to or in place of the nylon or polyester fibers.

While the physical properties of the fabric material and its constituents have been specified in the sample materials as aforesaid, it will be appreciated that those specific constituents result in a fabric material having fairly specific physical and absorptive properties. It is considered to be within the scope of this patent to adjust the specific parameters of the constituents to adapt to varying requirements such as more or less absorption or evaporation; overall material thickness (whether proportioned between the inner and outer layers or not) in the case where a more robust material is required, such as in the medical field applications or to enhance puncture resistance, or where more delicate material is desired, perhaps for use in lingerie. Furthermore, it will be appreciated that various fabric making techniques known to those skilled in the art may be employed for constructing the fabric layer which need not be limited to warp knit tricot and may include circular knit or other appropriate techniques. Accordingly, such modifications and variations are considered to be within the spirit and scope of the claims as appended.

We claim:

1. A composite fabric material (20) for absorbing and retaining fluid emitted from a body producing the fluid until evaporation thereof occurs, comprising:
   an absorbent first layer (22) for absorbing and retaining fluid emitted from a body producing the fluid, said first layer having a bare surface (28) through which said fluid is received, said first layer (22) comprising a fabric comprising acetate fibers and fibers of greater strength than said acetate fibers, said fabric being fabricated so that said acetate fibers are predominant on one side of the fabric and said fibers of greater strength are predominant on the other side of the fabric, said fabric being brushed on the one side on which the acetate fibers predominate; and
   a vapour permeable and liquid impervious second layer (24) of microporous polyurethane for preventing transmission of fluid absorbed and retained in the absorbent first layer therethrough, said second layer being adhered to the brushed side of said first layer so that the thickness of the composite fabric material (20) is in the range of about 0.5 to 1.5 mm, said second layer being adhered by an adhesive applied at discontinuous locations of the interface between said first and second layers so as to form between said fabric and said second layer a volume of open spaces and brushed fibers in which fluid received by said first layer is caused to be entrapped and by way of which evaporation of the received and entrapped fluid occurs through said second layer, and wherein said fabric being brushed is brushed sufficiently prior to being adhered to the second layer so as to provide the composite fabric material with a liquid absorption capacity of between about 3 and 9 g per g of material.

2. The composite fabric material as claimed in claim 1, wherein said fibers of greater strength have lower water absorbency than said acetate fibers.

3. The composite fabric material as claimed in claim 1, wherein said fibers of greater strength comprise polyester and/or nylon fibers.

4. The composite fabric material as claimed in claim 1, wherein said first layer fabric (22) is a warp knit tricot.

5. The composite fabric material as claimed in claim 1, wherein the ratio of said acetate fibers to said fibers of greater strength is about 5:1.

6. The composite fabric material as claimed in claim 1, wherein said first layer fabric (22) contains less than 25% by weight of said fibres of greater strength.

7. The composite fabric material as claimed in claim 1, wherein the thickness of said microporous polyurethane layer (24) is about 30 microns.

8. The composite fabric material as claimed in claim 1, wherein the pore sizes in said microporous polyurethane layer (24) are in the range of 0.1-10 μm.

9. The composite fabric material as claimed in claim 1, wherein said acetate fibers include an anti-microbial agent.

10. The composite fabric material as claimed in claim 1, wherein said first (22) and second layers (24) are adhered by a water insoluble, polyurethane-based adhesive (25).

11. The composite fabric material as claimed in claim 1, wherein said fabric (20) is launderable.

12. The composite fabric material as claimed in claim 1, wherein said fabric (20) is stain resistant.

13. An article for absorption and evaporation of bodily fluids made at least in part from the composite fabric material (20) of claim 1, said article selected from the group comprising undergarments, swimwear, bedding, linings and gussets for garments and undergarments, toilet training undergarments for children, incontinence undergarments, menstrual undergarments, nursing brassieres, and inserts for nursing brassieres.

14. An article of manufacture comprising a composite fabric material (20) as claimed in claim 1 to which is laminated, attached or otherwise adhered one or more further materials to the liquid impervious layer side of said composite material layer, each said further material disposed on the liquid impervious layer (24) side being vapor permeable.

15. A composite fabric material for use in articles of fluid absorptive clothing for drawing quantities of bodily fluids away from the body of a wearer and retaining them while they are permitted to be evaporated at least in part, said material comprising:
   an absorbent inner layer (22) having a bare surface (28) for receiving the bodily fluids, said inner layer comprising a fabric comprising acetate fibers and fibers of greater strength than said acetate fibers, said fabric being fabricated so that said acetate fibers are predominant on one side of the fabric and said fibers of greater strength are predominant on the other side of the fabric, and said inner layer being brushed on said one side so that brushed fibers extend from the fabric surface; and
   a vapour permeable and liquid impervious outer layer (24) of microporous polyurethane for preventing transmission of fluid absorbed and retained in the absorbent inner layer therethrough, said outer layer being adhered to the brushed side of said inner layer by an adhesive applied at discontinuous locations of the interface between said inner and outer layers so that the thickness of the composite fabric material is in the range of about 0.5 to 1.5 mm, said outer layer being adhered so as to form between the fabric surface and the outer layer a volume of open spaces and brushed fibers, and wherein said fabric being brushed is brushed sufficiently prior to being adhered to the outer layer so as to provide the composite fabric material with a liquid absorption capacity of between about 3 and 9 g per g of material,
   said inner layer (22) when contacted with the bodily fluids absorbing and retaining said bodily fluids in said fabric and within said volume while evaporation thereof occurs through said outer layer (24).

16. A composite fabric material for use in absorbent articles of manufacture for absorbing fluids and retaining them while they are permitted to be evaporated at least in part, said material comprising:
   an absorbent first layer (22) having a bare surface (28) for receiving the fluids, said first layer (22) comprising a fabric comprising acetate fibers and fibers of greater strength than said acetate fibers, said fabric being fabricated so that said acetate fibers are predominant on one side of the fabric and said fibers of greater strength are predominant on the other side of the fabric, said fabric being brushed on the one side on which the acetate fibers predominate so that brushed fibers extend from the fabric surface; and
   a vapour permeable and liquid impervious second layer (24) of microporous polyurethane for preventing transmission of fluid absorbed and retained in the absorbent first layer therethrough, said second layer being adhered to the brushed side of said first layer by an adhesive applied at discontinuous locations of the interface between said first and second layers so that the thickness of the composite fabric material is in the range of about 0.5 to 1.5 mm, said second layer being adhered so as to form between the fabric surface and the second layer a volume of open spaces and brushed fibers, and wherein said fabric being brushed is brushed sufficiently prior to being adhered to the second layer so as to provide the composite fabric material with a liquid absorption capacity of between about 3 and 9 g per g of material,
   said first layer (22) when contacted with the bodily fluid absorbing and retaining said bodily fluid in said fabric and within said volume while evaporation thereof occurs through said second layer (24).

17. The composite fabric material as claimed in claim 16, wherein said fibres of greater strength comprise nylon and/or polyester fibers.

18. The composite fabric material as claimed in claim 16, wherein said article of manufacture is selected from the group consisting of bedding, a liner for an item of clothing, a cover, and a gusset for an undergarment.

19. A fluid absorbent and retentive composite fabric material for absorbing fluids and retaining them while they are permitted to be evaporated at least in part, comprising an absorbent, fluid receiving first layer (22), said first layer comprising a fabric comprising acetate fibers and fibers from at least one other material, said fabric being fabricated so that said acetate fibers are predominant on one side of the fabric and being brushed on the one side on which the acetate fibers predominate; and
   a vapour permeable and liquid impervious second layer (24) for retaining fluids received and absorbed by said first layer and preventing transmission of said fluids therethrough while evaporation thereof occurs through said second layer, said second layer being adhered to the brushed side of said first layer by an adhesive applied at discontinuous locations of the interface between said first and second layers so that the thickness of the composite fabric material is in the range of about 0.5 to 1.5 mm, said outer layer being adhered so as to form a volume of open spaces and brushed fibers between said fabric and said second layer in which fluids received by said first layer are entrapped while evaporation thereof occurs through said second layer, and wherein said fabric being brushed is brushed sufficiently prior to being adhered to the second layer so as to provide the composite fabric material with a liquid absorption capacity of between about 3 and 9 g per g of material.

20. The composite fabric material as claimed in claim 19, wherein said at least one other material fibers are of greater strength than said acetate fibers.

21. The composite fabric material as claimed in claim 20, wherein said fibers of greater strength have lower water absorbency than said fibers.

22. The composite fabric material as claimed in claim 20, wherein said fibers of greater strength comprise polyester and/or nylon fibers.

23. The composite fabric material as claimed in claim 19, wherein said first layer fabric (22) is a warp knit tricot.

24. The composite fabric material as claimed in claim 19, wherein the ratio of said acetate fibers to said fibers of greater strength is about 5:1.

25. The composite fabric material as claimed in claim 20, wherein said first layer fabric contains less than 25% by weight of said fibers of greater strength.

26. The composite fabric material as claimed in claim 19, wherein said second layer (24) comprises microporous polyurethane.

27. The composite fabric material as claimed in claim 26, wherein the thickness of said microporous polyurethane layer (24) is about 30 microns.

28. The composite fabric material as claimed in claim 26, wherein the pore sizes in said microporous polyurethane layer (24) are in the range of 0.1-10 µm.

29. The composite fabric material as claimed in claim 19, wherein said acetate fibers include an anti-microbial agent.

30. The composite fabric material as claimed in claim 19, wherein said first and second layers (22,24) are adhered by a water insoluble, polyurethane-based adhesive (25).

31. The composite fabric material as claimed in claim 19, wherein said fabric (20) is launderable.

32. The composite fabric material as claimed in claim 19, wherein said fabric (20) is stain resistant.

33. The composite fabric material as claimed in claim 19, wherein said second layer (24) comprises hydrophilic polyurethane.

34. The composite fabric material as claimed in claim 19, characterized in that said material (20) has a liquid retention capacity under a 100 g centrifugal force of between about 0.32 and 0.35 g per g of material, and a thickness of between about 0.6 and 1.4 mm.

35. The fabric material of claim 34, further characterized in that said material (20) has a weight of between about 105 and 130 g/m$^2$.

36. The composite fabric material as claimed in claim 1, characterized in that said material (20) has a liquid retention capacity under a 100 g centrifugal force of between about 0.32 and 0.35 g per g of material, and a thickness of between about 0.6 and 1.4 mm.

37. The fabric material of claim 36, further characterized in that said material (20) has a weight of between about 105 and 130 g/m$^2$.

38. The composite fabric material as claimed in claim 1, wherein said first layer fabric is knitted so that said acetate fibers are predominant on the side of the fabric which is brushed and the fibers of greater strength are predominant on the bare face of the fabric material.

39. The composite fabric material as claimed in claim 20, wherein said first layer fabric is knitted so that said acetate fibers are predominant on the side of the fabric which is brushed and the fibers of greater strength are predominant on the opposite side.

* * * * *

UNITED STATES PATENT AND TRADEMARK OFFICE
CERTIFICATE OF CORRECTION

PATENT NO.       : 8,318,615 B1
APPLICATION NO.  : 10/149635
DATED            : November 27, 2012
INVENTOR(S)      : Filteau et al.

Page 1 of 1

It is certified that error appears in the above-identified patent and that said Letters Patent is hereby corrected as shown below:

Title page, after item (87) should read:

--(30)   Foreign Application Priority Data
Nov. 1, 1999    (CA) ........................ 2,289,313--

Signed and Sealed this
Fifth Day of February, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,318,615 B1 | Page 1 of 1 |
| APPLICATION NO. | : 10/149635 | |
| DATED | : November 27, 2012 | |
| INVENTOR(S) | : Filteau et al. | |

It is certified that error appears in the above-identified patent and that said Letters Patent is hereby corrected as shown below:

Title page, after item (87) should read:

--(30)   Foreign Application Priority Data
  Nov. 10, 1999   (CA) ........................ 2,289,313--

This certificate supersedes the Certificate of Correction issued February 5, 2013.

Signed and Sealed this
Thirty-first Day of December, 2013

Margaret A. Focarino
*Commissioner for Patents of the United States Patent and Trademark Office*